(12) United States Patent
Cianfrani et al.

(10) Patent No.: US 10,478,169 B2
(45) Date of Patent: Nov. 19, 2019

(54) TISSUE RETRACTOR AND METHOD OF USE

(71) Applicant: GLOBUS MEDICAL, INC., Audubon, PA (US)

(72) Inventors: Jason Cianfrani, East Norriton, PA (US); Mark Weiman, Coatesville, PA (US); Adam Friedrich, Cinnaminson, NJ (US); Erik Peterson, Pottstown, PA (US); Sean Suh, Morganville, NJ (US)

(73) Assignee: Globus Medical, Inc., Audubon, PA (US)

( * ) Notice: Subject to any disclaimer, the term of this patent is extended or adjusted under 35 U.S.C. 154(b) by 142 days.

(21) Appl. No.: 14/874,634

(22) Filed: Oct. 5, 2015

(65) Prior Publication Data

US 2016/0081683 A1 Mar. 24, 2016

Related U.S. Application Data

(63) Continuation of application No. 13/286,509, filed on Nov. 1, 2011, now Pat. No. 9,179,903, which is a continuation-in-part of application No. 12/722,100, filed on Mar. 11, 2010, now Pat. No. 8,353,826.

(51) Int. Cl.
*A61B 17/02* (2006.01)
*A61B 90/50* (2016.01)
*A61B 17/29* (2006.01)
*A61B 17/86* (2006.01)

(52) U.S. Cl.
CPC .......... *A61B 17/0206* (2013.01); *A61B 17/02* (2013.01); *A61B 17/8605* (2013.01); *A61B 90/50* (2016.02); *A61B 2017/2923* (2013.01)

(58) Field of Classification Search
CPC .................... A61B 17/0206; A61B 2017/0256
See application file for complete search history.

(56) References Cited

U.S. PATENT DOCUMENTS

| | | | |
|---|---|---|---|
| 3,749,088 A | 7/1973 | Kohlmann | |
| 6,139,493 A | 10/2000 | Koros et al. | |
| 6,869,398 B2* | 3/2005 | Obenchain | A61B 17/0206 600/210 |
| 7,850,608 B2 | 12/2010 | Hamada | |
| 8,636,655 B1* | 1/2014 | Childs | A61B 17/0206 600/219 |
| 8,974,381 B1* | 3/2015 | Lovell | A61B 17/0206 600/215 |
| 9,060,757 B2* | 6/2015 | Lawson | A61B 17/025 |

(Continued)

FOREIGN PATENT DOCUMENTS

| | | |
|---|---|---|
| DE | 202007012284 U1 | 10/2007 |
| JP | 2007-502175 A | 2/2007 |
| WO | 2006042241 A2 | 4/2006 |

*Primary Examiner* — Ellen C Hammond

(57) ABSTRACT

Systems, devices and methods related to retractor systems that retract tissue to allow access to a surgical site are described. The retractor systems can include a first rotatable arm attachable to a first blade, a second rotatable arm attachable to a second blade and a third linearly translatable arm attachable to a third blade. An attachment mechanism that is attachable to a fourth blade can be removably coupled to a mount on the frame. The retractors systems can also include two blade systems whereby when the retractor is in a closed configuration, the two blades form an oval opening.

8 Claims, 21 Drawing Sheets

(56) References Cited

U.S. PATENT DOCUMENTS

| | | | |
|---|---|---|---|
| 2003/0149341 A1* | 8/2003 | Clifton | A61B 17/0206 600/210 |
| 2005/0080320 A1 | 4/2005 | Lee et al. | |
| 2005/0137461 A1 | 6/2005 | Marchek et al. | |
| 2005/0234304 A1* | 10/2005 | Dewey | A61B 17/0206 600/210 |
| 2007/0208227 A1 | 9/2007 | Smith et al. | |
| 2008/0183046 A1 | 7/2008 | Boucher et al. | |
| 2008/0262318 A1* | 10/2008 | Gorek | A61B 17/0206 600/235 |
| 2010/0113885 A1 | 5/2010 | McBride et al. | |
| 2010/0152603 A1 | 6/2010 | Miles et al. | |
| 2010/0174148 A1 | 7/2010 | Miles et al. | |
| 2012/0245431 A1* | 9/2012 | Baudouin | A61B 17/0206 600/213 |
| 2012/0303034 A1* | 11/2012 | Woolley | A61B 17/0206 606/90 |
| 2013/0190575 A1* | 7/2013 | Mast | A61B 17/7079 600/215 |
| 2014/0066718 A1* | 3/2014 | Fiechter | A61B 17/0206 600/214 |
| 2015/0313585 A1* | 11/2015 | Abidin | A61B 17/0206 600/213 |
| 2016/0074029 A1* | 3/2016 | O'Connell et al. | A61B 17/0206 600/213 |
| 2016/0106408 A1* | 4/2016 | Ponmudi | A61B 17/025 606/90 |

\* cited by examiner

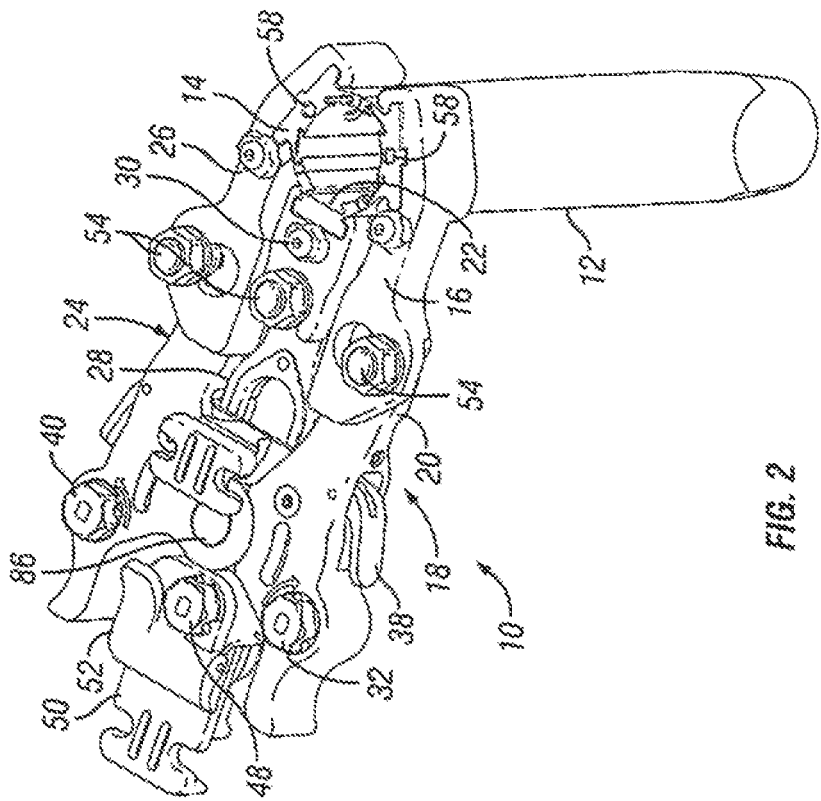
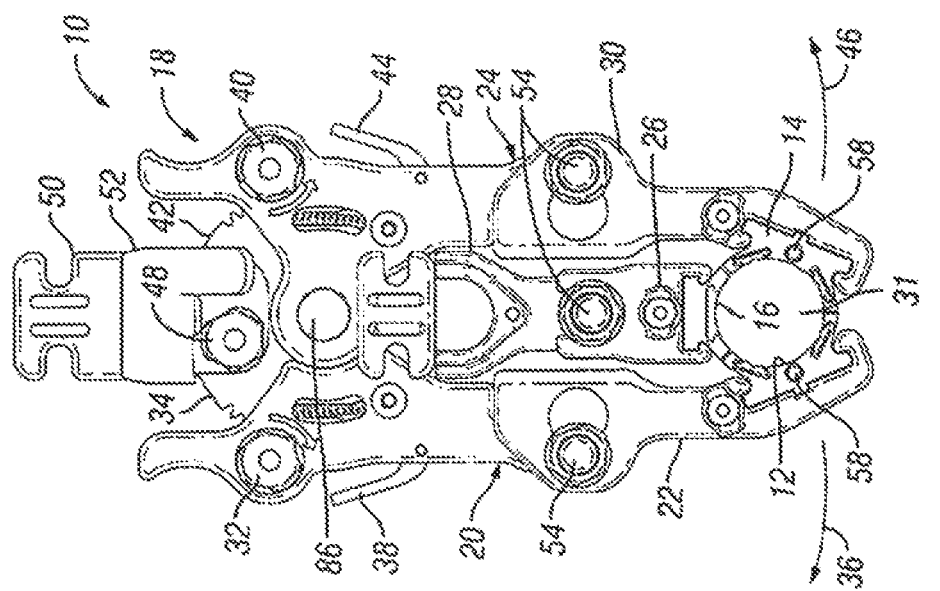

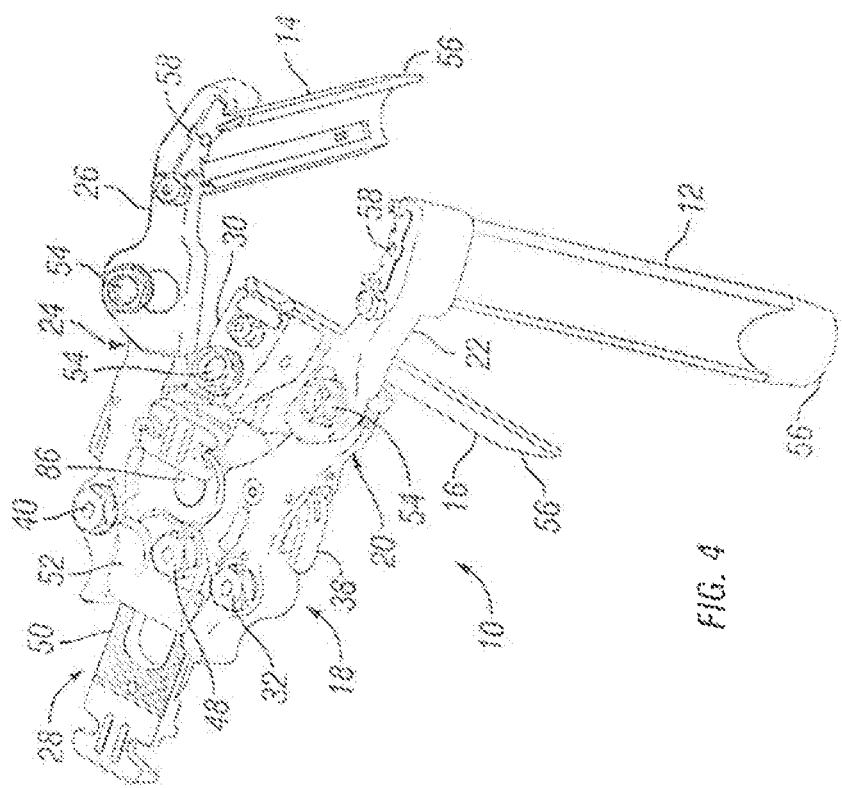

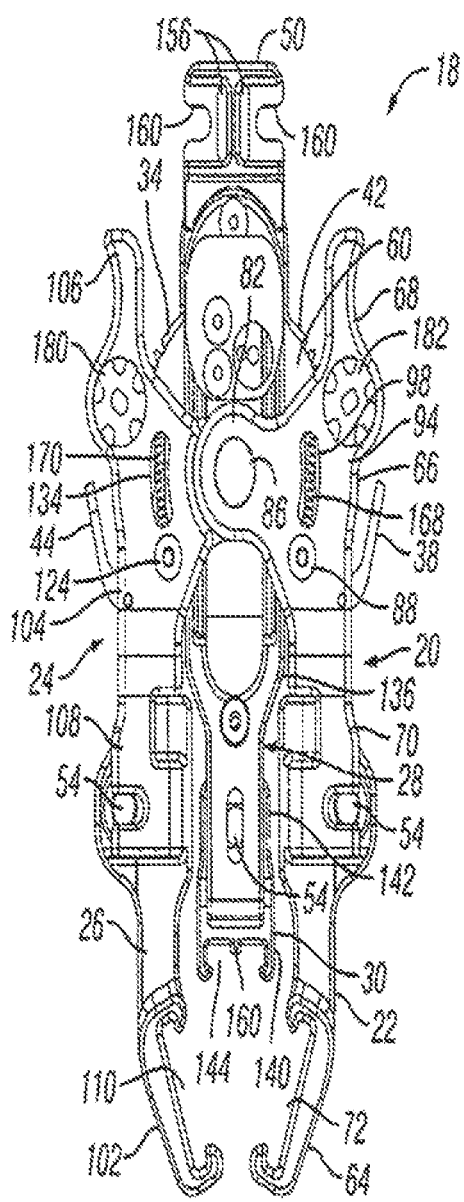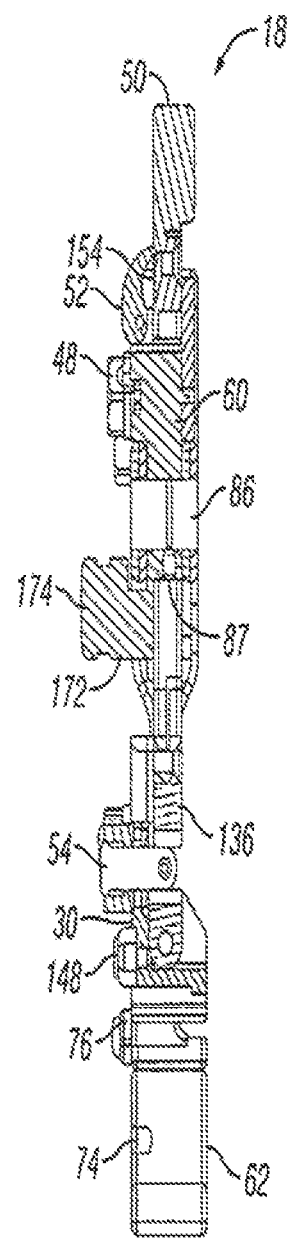
FIG. 9
FIG. 10

TISSUE RETRACTOR AND METHOD OF USE

CROSS REFERENCE TO RELATED APPLICATIONS

This Patent Application is continuation of U.S. patent application Ser. No. 13/286,509 filed on Nov. 1, 2011 which is a continuation-in-part application claiming priority to U.S. patent application Ser. No. 12/722,100, now U.S. Pat. No. 8,353,826 filed on Mar. 11, 2010, the entire contents of which are incorporated by reference.

FIELD OF THE INVENTION

The present disclosure generally relates to medical devices. In particular, in one or more embodiments, the present disclosure relates to methods and devices for retracting tissue in a surgical procedure to allow access to the surgical site.

BACKGROUND OF THE INVENTION

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray. One typical retractor system may include a plurality of blades coupled to a retractor frame. In use, the blades may be inserted into an incision and then retracted to displace tissue surrounding the incision down to the surgical site. To minimize trauma to the tissue, this tissue displacement should generally be refined and controlled. However, current retractor systems may not provide desired control of the distraction.

Thus, there is a need for improved methods and devices that can be used for retracting tissue to provide access to the surgical site.

SUMMARY OF THE INVENTION

Systems, devices and methods related to multi-blade retractor systems are described below. In some embodiments, a multi-blade retractor system comprises a retractor frame comprising a first arm, a second arm, and a third arm coupled to the first and second arms; a first blade coupled to a distal end of the first arm; a second blade coupled to a distal end of the second arm; a third blade coupled to a distal end of the third arm; and a removable attachment mechanism capable of attaching to the retractor frame, wherein the attachment mechanism includes an additional blade to attach to the retractor frame.

In some embodiments, a multi-blade retractor system comprises a retractor frame comprising a first rotatable arm and a second rotatable arm; a first blade coupled to a distal end of the first rotatable arm; a second blade coupled to a distal end of the second rotatable arm; and an attachment mechanism capable of attaching to the retractor frame, wherein the attachment mechanism is capable of adding an additional blade to attach to the retractor frame.

In some embodiments, a multi-blade retractor system comprises a retractor frame comprising a first arm and a second arm; a first blade coupled to the distal end of the first arm; and a second blade coupled to the distal end of the second arm, wherein in a closed configuration, the first blade and the second blade form an oval shaped opening.

BRIEF DESCRIPTION OF THE DRAWINGS

These drawings illustrate certain aspects of the present invention and should not be used to limit or define the invention.

FIGS. 1 and 2 illustrate a retractor system in a closed configuration in accordance with some embodiments.

FIGS. 3 and 4 illustrate a retractor system in an open configuration in accordance with some embodiments.

FIG. 9 is a bottom view of a retractor frame in accordance with some embodiments.

FIG. 10 is a cross-sectional view of a retractor frame in accordance with some embodiments.

DETAILED DESCRIPTION OF THE ILLUSTRATED EMBODIMENTS

Figure 5:
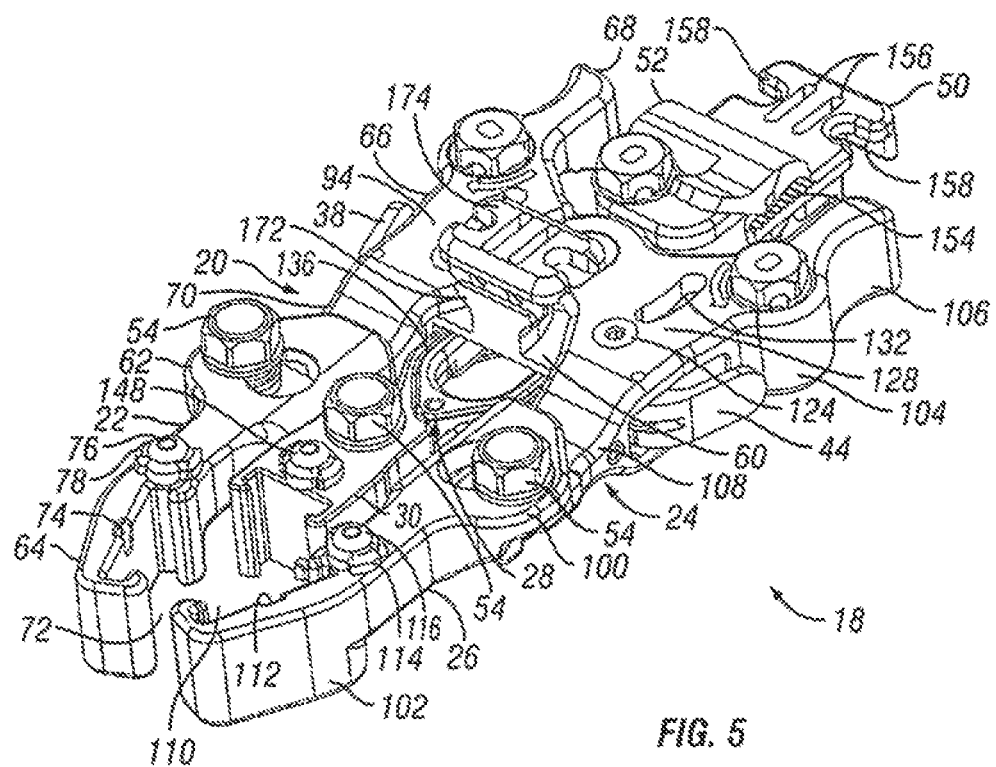
FIG. 5 illustrates a retractor frame in accordance with some embodiments.
Figure 6:
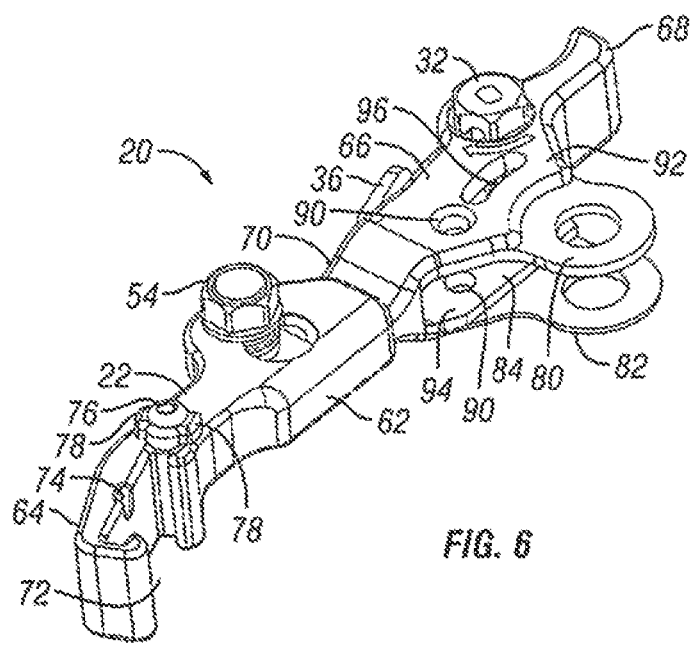
FIG. 6 illustrates a rotatable arm for use in a retractor system in accordance with some embodiments.
Figure 7:
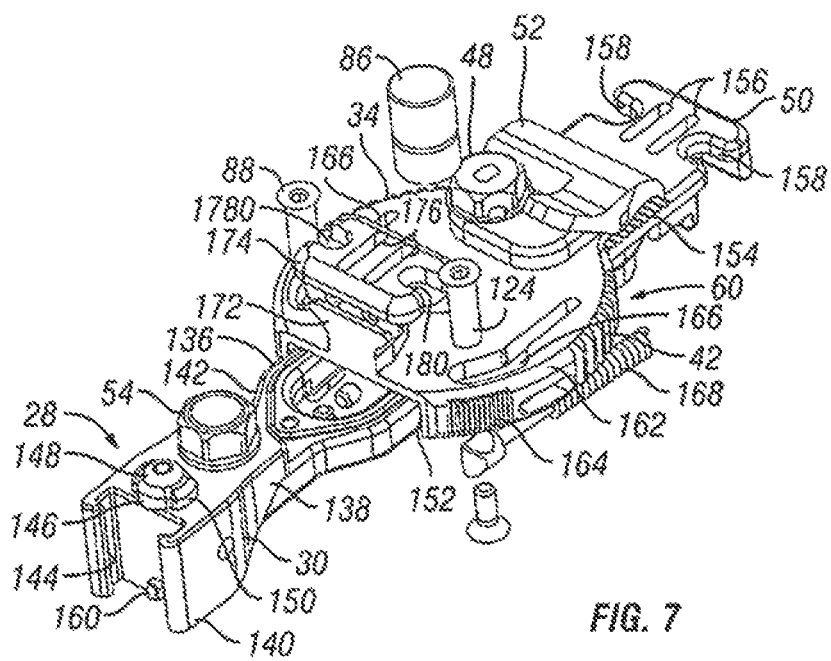
FIG. 7 illustrates a linearly translatable arm and a central gear housing for use in a retractor system in accordance with some embodiments.
Figure 8:
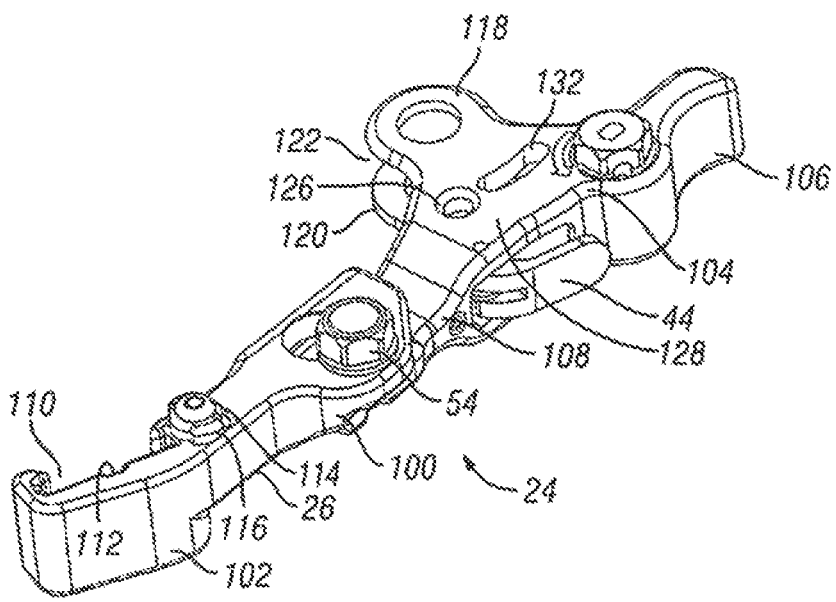
FIG. 8 illustrates a rotatable arm for use in a retractor system in accordance with one some embodiments.

FIGS. 1-4 illustrate a retractor system 10 that may be used to retract tissue in a surgical procedure in accordance with one embodiment of the present invention. The retractor system 10 comprises a first blade 12, a second blade 14, and a third blade 16. The first, second, and third blades 12, 14, 16 are each coupled to a retractor frame 18. The retractor frame 18 comprises a first rotatable arm 20 having a first blade attachment member 22 for holding and positioning the first blade 12. The retractor frame 18 further comprises a second rotatable arm 24 having a second blade attachment member 26 for holding and positioning the second blade 14. The retractor frame 18 further comprises a linearly translatable arm 28 having a third blade attachment member 30 for holding and positioning the third blade 16. The first and second rotatable arms 20, 24 and the linearly translatable arm 28 may be actuated so that the blades 12, 14, 16 may be separated a desired distance from each other. In addition, the blade attachment members 22, 26, and 30 may be actuated to angulate the blades 12, 14, 16, increasing the distance between the distal ends of the blades 12, 14, 16. In this manner, tissue surrounding an incision may be retracted providing access to the surgical site. In embodiments, the first, second, and third blades 12, 14, 16 may be individually actuated.

FIGS. 1-2 illustrate the retractor system 10 in a "closed" or non-retracted configuration, in accordance with one embodiment of the present invention. In the closed configuration, the first, second, and third blades 12, 14, 16 are radially disposed around a central bore 31 to form a substantially closed, tube-shaped structure.

FIGS. 3-4 illustrate the retractor system 10 in an "open" or retracted configuration, in accordance with one embodiment of the present invention. In the open configuration, the first, second, and third blades 12, 14, 16 have been moved so that they no longer form a tube-shaped structure that is substantially closed. Rather, the first and second blades 12, 14 have been rotated and angulated and third blade 16 has been linearly translated and angulated to enlarge the diameter of the central bore about which the blades 12, 14, 16 are arranged.

The first rotatable arm 20 may be actuated by rotation of an actuator 32. The actuator 32 may be a fastener, such as a hex screw (e.g., a 10 mm hex screw). The actuator 32 may be coupled to a planetary gear 180 (shown on FIG. 9) having teeth that engage a first sun gear 34. The engagement between the actuator 32, the planetary gear 180, and the first sun gear 34 may be described as a planetary gear mechanism in accordance with embodiments of the present invention. In the illustrated embodiments, a ratchet-locking mechanism 38 is included that engages teeth on the first sun gear 34. As the actuator 32 is turned, the first rotatable arm 20 should rotate as indicated by arrow 36 with the distal end of the arm 20 moving in an arc. For example, rotation of the actuator 32 in the counter-clockwise direction drives rotation of the first rotatable arm 20 as indicated by arrow 36 thereby rotating the first blade 12 in an arc away from the second and third blades 14, 16. In an embodiment, the first sun gear 34 is stationary with the planetary gear 180 rotating tooth by tooth along the first sun gear 34. In an embodiment, the ratchet-locking mechanism 38 engages the first sun gear 34 to prevent rotation of the first rotatable arm 20 in the counter-clockwise direction. The first rotatable arm 20 may be released from its rotated state (FIGS. 3-4) by depressing the lever of the ratchet-locking mechanism 38 to allow the first rotatable arm 20 to rotate back to its initial position (FIGS. 1-2).

In a similar manner to the first rotatable arm 20, the second rotatable arm 24 may be actuated by rotation of an actuator 40. The actuator 40 may be, for example, a fastener, such as a hex screw (e.g., a 10 mm hex screw). The actuator 40 may be coupled to a planetary gear 182 (shown on FIG. 9) having teeth that engage a second sun gear 42. The engagement between the actuator 40, the planetary gear 182, and the second sun gear 42 may be described as a planetary gear mechanism in accordance with embodiments of the present invention. It should be understood that use of the term "sun" is not meant to imply that the first and second sun gears 34, 42 are circular in shape but rather that the gears function in conjunction with the other components in a manner similar to what is commonly referred to as a planetary gear. In the illustrated embodiment, a ratchet-locking mechanism 44 is included that engages teeth on the second sun gear 42. As the actuator 40 is turned, the second rotatable arm 24 should rotate as indicated by arrow 46 with the distal end of the second rotatable arm 24 moving in an arc. For example, rotation of the actuator 40 in the counter-clockwise direction should drive rotation of the second rotatable arm 24 as indicated by arrow 46 thereby rotating the second blade 14 in an arc away from the first and third blades 12, 16. In an embodiment, the second sun gear 42 is stationary with the planetary gear 182 rotating tooth by tooth along the second sun gear 42. In an embodiment, the ratchet-locking mechanism 44 engages the second sun gear 42 to prevent rotation of the second rotatable arm 24 in the counter-clockwise direction. The second rotatable arm 24 may be released from its rotated state (FIGS. 3-4) by depressing the lever of the ratchet-locking mechanism 44 to allow the second rotatable arm 24 to rotate back to its initial position (FIGS. 1-2).

The linearly translatable arm 28 may be actuated by rotation of an actuator 48. The actuator 48 may be, for example, a fastener, such as a hex screw (e.g., a 10 mm hex screw). The actuator 48 may be coupled to a pinion gear (not shown) that engages teeth on rack portion 50 of the linearly translatable arm 28. As illustrated, the rack portion 50 may be on the opposite end of the linearly translatable arm 28 from the third blade attachment member 30. The engagement between the actuator 48, the pinion gear, and the rack portion 50 may be described as a rack and pinion gear mechanism in accordance with embodiments of the present invention. In the illustrated embodiment, ratchet-locking mechanism 52 is also included that engages teeth on the rack portion 50. As the actuator 48 is turned, the linearly translatable arm 28 moves in a line as illustrated in FIGS. 3-4. This will increase the distance between the third blade 16 and the first and second blades 12, 14. In an embodiment, the ratchet-locking mechanism 42 engages the rack portion 50 to prevent translation in the opposite direction that would shorten the distance between the blades 12, 14, 16. The linearly translatable arm 28 may be released from its translated state (FIGS. 3-4) by depressing the lever of the ratchet-locking mechanism 52 to allow the linearly translatable arm 28 to rotate back to its initial position (FIGS. 1-2) without having to turn the actuator 48.

In accordance with present embodiments, the first, second, and third blades 12, 14, 16 may be angulated by respective rotation of actuators 54. As used herein, angulation of the blades 12, 14, 16 refers to rotation of the distal ends of the blades 12, 14, 16 outwardly and upwardly, resulting in separation of the distal ends. The actuators 54 may be, for example, a fastener, such as a hex screws (e.g., 10 mm hex screws). As illustrated by FIGS. 3-4, each of the actuators 54 may be rotated to angulate the first, second, and third blades 12, 14, 16, respectively. As will be discussed in more detailed with respect to FIG. 13, rotation of the actuators 54 facilitates this angulation by angulating the blade attachment members 22, 26, 30 to cause corresponding angulation of the blades 12, 14, 16. In an embodiment, the angulation used is an infinite angle adjustment mechanism that is controlled by threading.

The first, second, and third blades 12, 14, 16 of the retractor system 10 may have one or more holes 58 extending through the blades 12, 14, 16 along their respective long axes. The holes 58 may configured to allow passage of light components, k-wires, or other suitable instruments through the blades 12, 14, 16. The edges of the blades may be rounded, for example, to minimize the risk of damage to the retracted tissue. While illustrated with three blades, those of ordinary skill in the art will appreciate the retractor system 10 may include more, or less, than three blades configured to move as desired for a particular application. For example, a retractor system may be used that comprises four blades with two linearly translatable arms and two rotatable arms. Alternatively, a retractor may be used that comprises two rotatable arms or alternatively one linearly translatable arm and one rotatable arm.

It should be understood that the actuators 32, 40, 48, 54 may be configured to engage a variety of different tools to facilitate the desired rotation. For example, wrenches, screwdrivers, or any other suitable tools may be used to rotate the actuators 32, 40, 48, 54. In addition, while actuators 32, 40, 48, 54 are shown as fasteners, it should be understood that fasteners are not required to facilitate the movement. Other suitable devices, such as cranks, may be used to facilitate the desired movement.

An embodiment of the present invention includes using the retractor system 10 to retract tissue in a surgical procedure. For example, the retractor system 10 may be placed into an opening (e.g., an incision) in the patient's tissue with the retractor system 10 in the closed position. The surgeon (or other operator) may then separately rotate actuator 32 and actuator 40 to rotate the first rotatable arm 20 and the second rotatable arm 24, respectively, thus moving the first and second blades 12, 14 in an arc. The surgeon may also rotate actuator 48 to move the linearly translatable arm 28 and, thus, the third blade 16, in a line. In this manner, the first, second, and third blades 12, 14, 16 may be retracted (or spread) to provide enhanced access to the surgical site. To further enhance access, the surgeon may rotate each of actuators 54 to angulate the first, second, and third blades 12, 14, 16.

Turning now to FIGS. 5-11, the retractor frame 18 is illustrated in more detail in accordance with embodiments of the present invention. As previously mentioned, the retractor frame 18 may comprise a first rotatable arm 20, a second rotatable arm 24, and a linearly translatable arm 28. A portion of the second rotatable arm 24 is removed on FIG. 11 to illustrate interior components of the retractor frame 18. In addition, the retractor frame 18 may further comprise a central gear housing 60. As illustrated, the central gear housing 60 houses the first sun gear 34 and the second sun gear 42. In accordance with present embodiments, the first sun gear 34 and the second sun gear 42 are configured to facilitate rotation of the first rotatable arm 20 and the second rotatable arm 24, respectively.

The first rotatable arm 20 may comprise a first blade attachment member 22 having a proximal end 62 and a distal end 64. The first rotatable arm 20 may further comprise a base portion 66 having a proximal end 68 and a distal end 70. The proximal end 62 of the first blade attachment member 22 may be disposed over the distal end 70 of the base portion 66. The first blade attachment member 22 may be secured to the base portion 66 by a pivot pin (not shown). The distal end 64 of the first blade attachment member 22 may be configured to receive the first blade 12 (illustrated on FIGS. 1 and 3). For example, the distal end 64 may have a slot 72 that receives the first blade 12. A notch 74 in the distal end 64 may receive a corresponding protrusion in the first blade 12. Fastener 76 may secure the first blade 12 in the blade attachment member 22. As illustrated, the fastener 76 may include one or more radially extending protrusions 78. To secure the first blade 12, the first blade 12 may be inserted into slot 72 until the protruding portion of the blade 12 lands on the notch 74. The fastener 76 may be rotated until one of the protrusions 78 extends over the top of the first blade 12 to prevent its removal from the slot 72.

The base portion 66 may have a finger grip at the proximal end 68 that may be used to facilitate a controlled return of the first rotatable arm 20 after depression of the ratchet-locking mechanism 38. Top and bottom annular-shaped members 80, 82 may extend laterally from the first rotatable arm 22. Slot 84 may be formed in the first rotatable arm 20 for receiving the central gear housing 60. Pin 86 may extend through the annular-shaped members 80, 82 to secure the central gear housing 60 in the slot 84 with the teeth of the first sun gear 34 engaging the planetary gear 180. Set screw 87 should secure the pin 88 in the central gear housing 60. Pin 88 may extend through holes 90 in the upper and lower portions 92, 94 of the base portion 66. Pin 88 should be coupled to spring 170 for spring-loading the first rotatable arm 20. Upper slot 96 may be formed in the upper portion 92 of the base portion 66 to provide access to the central gear housing 60 and other components of the retractor frame 18. As illustrated by FIG. 9, there may be a corresponding lower slot 98 formed in the lower portion 94 of the base portion 66 that can provide access to the central gear housing 60 and other components of the retractor frame 18.

The second rotatable arm 24 may comprise a second blade attachment member 26 having a proximal end 100 and a distal end 102. The second rotatable arm 24 may further comprise a base portion 104 having a proximal end 106 and a distal end 108. The proximal end 100 of the second blade attachment member 26 may be disposed over the distal end 108 of the base portion 104. The second blade attachment member 26 may be secured to the base portion 104 by a pivot pin 105 (shown on FIG. 12). The distal end 102 of the second blade attachment member 26 may be configured to receive the second blade 14 (illustrated on FIGS. 1 and 3). For example, the distal end 102 may have a slot 110 that receives the second blade 14. A notch 112 in the distal end 102 may receive a corresponding protrusion in the second blade 14. Fastener 114 may secure the second blade 14 in the second attachment member 26. As illustrated, the fastener 114 may include one or more radially extending protrusions 116. To secure the second blade 14, it may be inserted into slot 110 until the protruding portion of the blade 14 lands on the notch 112. The fastener 114 may then be rotated until one of the protrusions 116 extends over the top of the second blade 14 to prevent its removal from the slot 110.

The base portion 104 may have a finger grip at the proximal end 106 that may be used to facilitate a controlled return of the second rotatable arm 24 after depression of the ratchet-locking mechanism 38. Top and bottom annular-shaped members 118, 120 may extend laterally from the second rotatable arm 26. Slot 122 may be formed in the second rotatable arm 24 for receiving the central gear housing 60. Pin 86 may extend through the annular-shaped members 118, 120 to secure the central gear housing 60 in the slot 122 with the teeth of the second sun gear 42 engaging the planetary gear 182. Pin 124 may extend through holes 126 in the upper and lower portions 128, 130 of the base portion 104. Pin 124 should be coupled to spring 168 for spring-loading the second rotatable arm 24. Upper slot 132 may be formed in the upper portion 128 of the base portion 104 to provide access to the central gear housing 60 and other components of the retractor frame 18. As illustrated by FIG. 9, there is a corresponding lower slot 134 formed in the lower portion 130 of the base portion 104 that can provide access to the central gear housing 60 and other components of the retractor frame 18.

The linearly translatable arm 28 may comprise a third blade attachment member 30 and a rack portion 50 separated from third blade attachment member 30 by a slotted middle portion 136. In an embodiment, the rack portion 50 may be at least partially slotted. The third blade attachment member 30 may have a proximal end 138 and distal end 140. The slotted middle portion 136 may comprise a distal end 142 on which the proximal end 138 of the third blade attachment member 30 may be disposed. A pin may secure the third blade attachment member 30 to the slotted middle portion 136. The distal end 140 of the third blade attachment member 30 may be configured to receive the third blade 16 (illustrated on FIGS. 1 and 3). For example, the distal end 140 may have a slot 144 that receives the third blade 16. A notch 146 in the distal end 140 may receive a corresponding protrusion in the third blade 16. Fastener 148 may secure the third blade 16 in the third blade attachment member 30. As illustrated, the fastener 148 may include one or more radially extending protrusions 150. To secure the third blade 16, it may be inserted into slot 144 until the protruding portion of the blade 16 lands on the notch 146. The fastener 148 may then be rotated until one of the protrusions 150 extends over the top of the third blade 16 to prevent its removal from the slot 144. A protrusion 160 in the bottom of the slot 144 may further secure the third blade 16 in the slot 144.

The slotted middle portion 136 may be coupled to the third blade attachment member 30 at its distal end 142 with the rack portion 50 on its other end. As illustrated, the slotted middle portion 136 may extend into a through passageway 152 in the central gear housing 60. The slotted middle portion 136 separates the rack portion 50 from the third blade attachment member 30. As illustrated, the rack portion 50 may extend from the through passageway 152 in the central gear housing 60. The rack portion 50 may further comprise rack teeth 153 that should engage with the actuator/pinion gear 48. Ratchet-locking mechanism 52 may further engage teeth 154 on the rack portion 50. The rack portion 50 may further comprise features for securing the retractor system 10 to an arm (not illustrated). Those of ordinary skill in the art should understand that the arm may be used to provide, for example, a connection between the retractor system 10 and an operating table. The features for securing the retractor system 10 to the arm may include, for example, a pair of slots 156 and semi-elliptical openings 158 on opposing sides of the rack portion 50.

The central gear housing 60 may comprise a first sun gear 34 on a first side and a second sun gear 42 on a second side. In the illustrated embodiment, the central gear housing 60 is generally disc shaped with a rim 162 about which the first sun gear 34 and the second sun gear 42 are individually rotatable. As illustrated, the rim 162 may further comprise teeth 164 that engage the ratchet-locking mechanism 44 of the second rotatable arm 24. While not illustrated, there may be corresponding teeth on the opposite side of the rim 162 for engaging the ratchet-locking mechanism 38 for the first rotatable arm 20. A central opening may be disposed in the central gear housing 60 through which pin 86 may be inserted. Central gear housing 60 may further comprise a through passageway 152 having a rectangular cross section. Central gear housing 60 may further comprise channels 166. In the illustrated embodiment, spring 170 may be coupled to pin 88 for providing the force to return the first rotatable arm 20 to its initial position when the ratchet-locking mechanism 38 is released. As further illustrated, pin 124 may be inserted into the other one of the channels 166. Spring 168 may be coupled to pin 124 for providing force to return the second rotatable arm 24 to its initial position when the ratchet-locking mechanism 44 is released. Central gear housing 60 may further comprise upwardly extending arm 172 to which arm attachment plate 174 may be attached. Arm attachment plate 174 may comprise features for attaching the retractor system 10 to a table connector, such as an arm. For example, arm attachment plate 174 may comprise slots 176 and semi-elliptical openings 178. As illustrated, ratchet-locking mechanism 52 may be coupled to the central gear housing 60 so as to engage teeth 154 on the rack portion 50 of the linearly translatable arm 28. As further illustrated, actuator 48 may extend through an opening in the central gear housing 60 so that a connected pinion gear (not illustrated) also engages the rack teeth 153.

Figure 12:
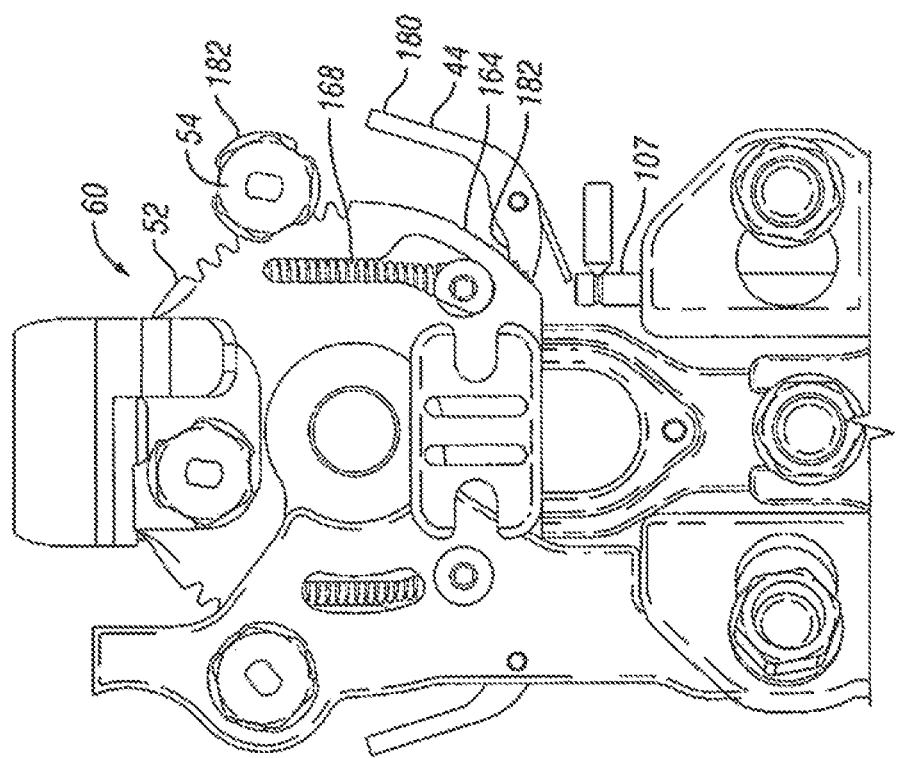
FIG. 12 illustrates a ratchet-locking mechanism in accordance with some embodiments
Figure 11:
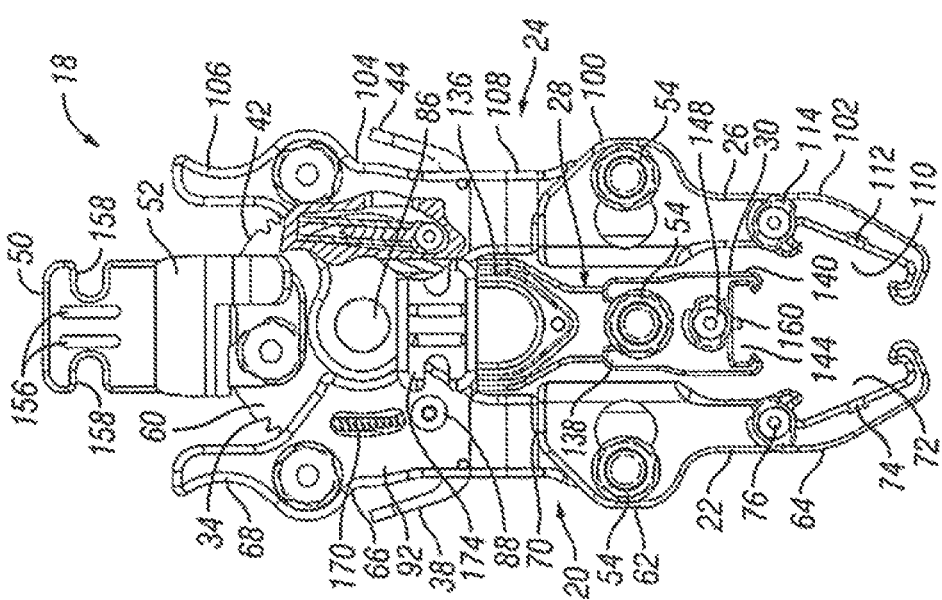
FIG. 11 is a top view of a retractor frame in accordance with some embodiments.

FIG. 12 illustrates the ratchet-locking mechanism 44 in more detail in accordance with one embodiment of the present invention. In an embodiment, the ratchet-locking mechanism 44 includes a lever 180 and a nose 182. As illustrated, the nose 182 of the ratchet-locking mechanism 44 engages teeth 164 on the central gear housing 60. As previously discussed, rotation of the actuator 54 in the counter-clockwise direction should drive the planetary gear 182 tooth by tooth along the second sun gear 52. Rotation of the actuator 54 should drive corresponding rotation of the second rotatable arm 24 in the counter-clockwise direction. The nose 182 of the ratchet-locking mechanism 44 should engage the teeth 164 of the second sun gear 52 to allow movement of the second rotatable arm 24 in one direction, i.e., the counter-clockwise direction. The second rotatable arm 24 can be released from this rotated position by depressing the lever 180. The spring 168 should generally provide the force need to return the second rotatable arm 24 to its initial position when the lever 180 is released. While the previous discussion of FIG. 12 is with respect to the ratchet-locking mechanism 44, it should be understood that ratchet-locking mechanism 38 may be operated in a similar manner to restrict rotation of the first rotatable arm 20. It should further be noted that, while the previous discussion describes a ratchet-locking mechanism, other suitable devices for allowing movement of the rotatable arms in one direction may be used in accordance with the present invention.

Figure 13:
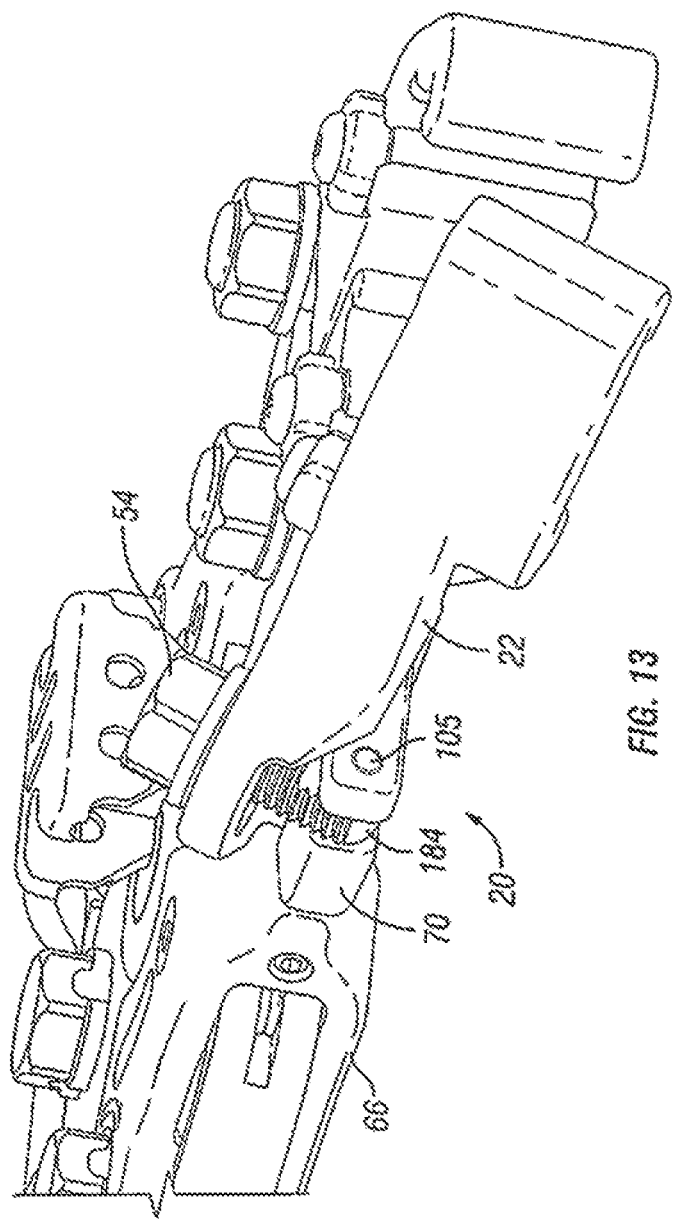
FIG. 13 illustrates angulation of a retractor blade in accordance with some embodiments.

FIG. 13 describes angulation of the blade attachment member 22 in accordance with one embodiment of the present invention. As previously discussed, the first rotatable arm 20 comprises blade attachment member 22 coupled to the distal end 70 of the base portion 66. As illustrated, actuator 54 may secure the blade attachment member 22 onto the base portion 66. The actuator 54 may be threaded, for example, into a corresponding opening 184 in the base portion 66. The pin 107 (See FIG. 12) pivotably connects the attachment member 22 to the screw shaft of the actuator 54. A second pin 105 (See FIG. 13) connects the attachment member 22 through the base portion of the 66. The screw head of the actuator is provided with a portion that allows the attachment member to be retained within the head portion of the actuator and is pivotally rotatable when the actuator 54 is manipulated. The pin 107 and pin 105 create two separate axis of rotations. As the actuator is manipulated the attachment member 22 is rotated along the axis of rotation of pin 105. In an embodiment, the opening 184 may be angled, in that the axis of the opening 184 may be at an angle with respect to the z-axis of the first rotatable arm 20. Accordingly, as the actuator 54 is rotated, the blade attachment member 22 should pivot. In this manner, the blade attachment member 22 and, thus, the first blade 12 may be angulated. While the previous discussion of FIG. 12 and FIG. 13 is with respect to angulation of the first blade attachment member 22, it should be understood that second and third blade attachment members 26, 30 may be angulated in a similar manner. It should further be noted that, while the previous discussion describes an angled actuator for angulating the blade attachment member 22, 26, and 30, other suitable mechanisms for facilitating the desired blade angulation may be used in accordance with the present invention.

Additional Embodiments of Retractor Systems

Additional embodiments of retractor systems are discussed below. These systems encompass different mechanisms for opening and closing the retractors, as well as different components for attaching to the retractors.

Figure 14:
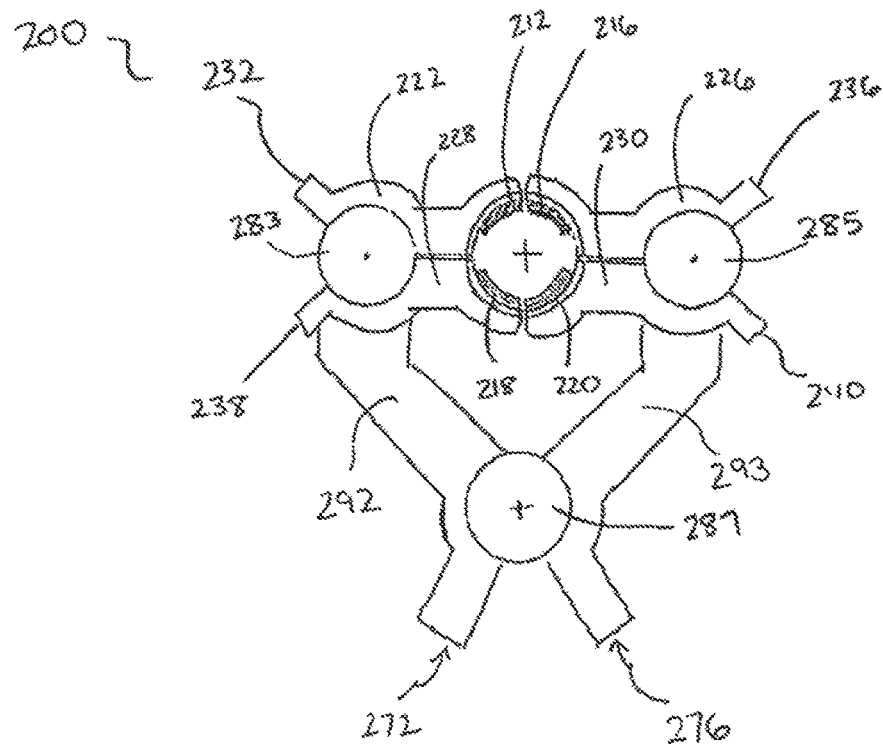
FIG. 14 illustrates a top view of an alternative retractor system with four blades in a closed configuration in accordance with some embodiments.

FIG. 14 illustrates a top view of an alternative retractor system with four blades in a closed configuration in accordance with some embodiments. The retractor system 200 includes four arms 222, 226, 228 and 230. The arms include proximal sections 232, 236, 238 and 240 and distal sections 242, 246, 248 and 250 respectively. The distal sections of the arms are capable of outward expansion to facilitate tissue retraction, as shown in FIG. 15.

Each of the arms 222, 226, 228 and 230 are operably connected to individual blades 212, 216, 218 and 220. The blades 212, 216, 218 and 220 are configured to be slidable relative to an inner wall of their respective arms. As the distal sections 242, 246, 248 and 250 expand outwardly, the blades 212, 216, 218 and 220 slide outwardly from the arms, thereby helping to expand the area of tissue retraction as discussed further below.

In some embodiments, the blades comprise extensions that are continuous without slots or perforations, while in other embodiments, the blades comprise extensions that include slots and/or perforations. In some embodiments, the blades are formed of stainless steel, titanium, or metallic alloy. The blades can also include one or more polymeric materials. The blades can also be formed of or coated with a radiolucent or semi-radiolucent material to assist in x-ray procedures. In some embodiments, the distal portions of the blades can be smooth and curved, while in other embodiments, the distal portions can be toothed or combed.

Figure 15:
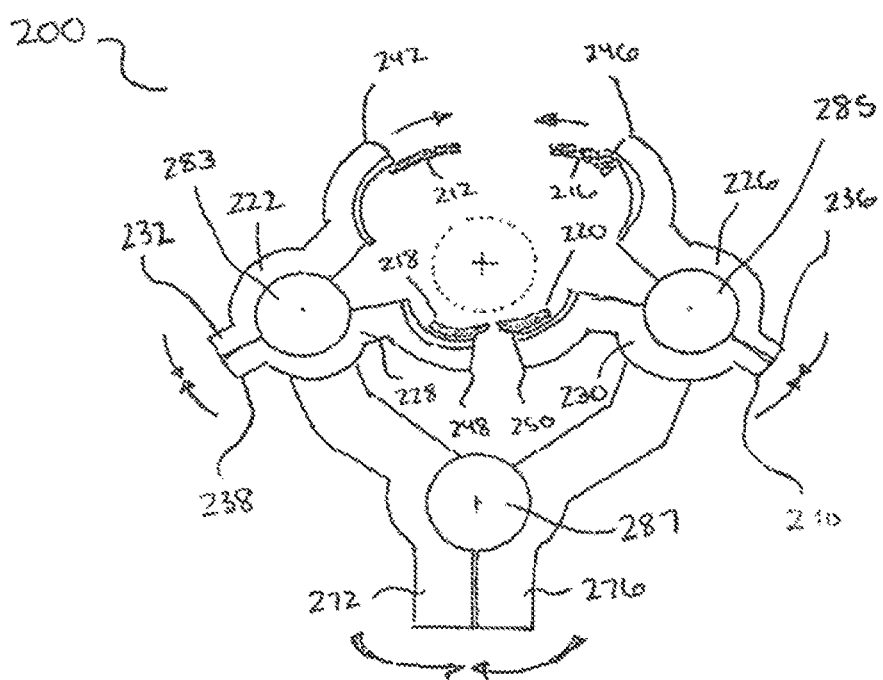
FIG. 15 illustrates a top view of the retractor system in FIG. 14 in an open configuration in accordance with some embodiments.

FIG. 15 illustrates a top view of the retractor in FIG. 14 in an open configuration in accordance with some embodiments. In this figure, the distal sections 242, 246, 248 and 250 of the arms have been expanded outwardly, while the proximal sections 232, 236, 238 and 240 have been brought closer together. To facilitate this movement, the retractor can include one or more actuators 283, 285 that when actuated (e.g., pressed, turned or rotated), cause expansion or contraction of the arms. For example, as shown in FIG. 15, rotation of actuator 283 can cause the distal sections 242, 248 of arms 222, 228 to expand outwardly, while rotation of actuator 285 can cause the distal sections 246, 250 of arms 226, 230 to expand outwardly. In some embodiments, arms 222 and 228 can hinge around actuator 283, while arms 226 and 230 hinge around actuator 285. A third actuator 287 can also be provided to expand and/or contract arms 292 and 293, thereby further helping to expand the tissue retracted area.

As shown in FIG. 15, the retractor blades slide outwardly relative to their respective arms during expansion. As the blades slide outwardly, they proceed to push tissue back and create a larger retraction area through which a surgical procedure can be performed. In some embodiments, the blades can be angled or tilted outwardly to provide a large visualization field into a surgical site. While the illustrated embodiment illustrates four retractor blades, in other embodiments, more or less than four blades can be operated in a similar manner. For example, in another embodiment, a retractor blade having six blades can be provided to expand in a similar manner.

Figure 16:
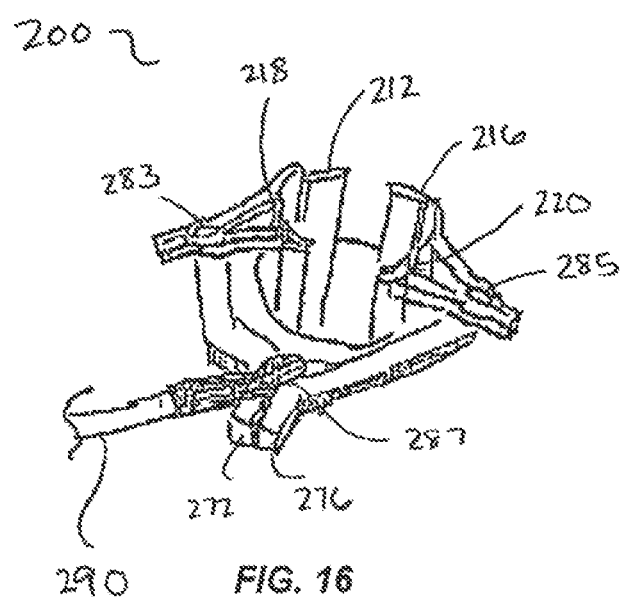
FIG. 16 illustrates a perspective view of a retractor system comprising the retractor in FIG. 14 in an open configuration and an instrument in accordance with some embodiments.

FIG. 16 illustrates a perspective view of a retractor system comprising the retractor in FIG. 14 and an instrument in accordance with some embodiments. As shown in the figure, the instrument 290 is configured to rotate the actuator 287. The same instrument 290 can be used to rotate the other actuators 283 and 285 as well. In other embodiments, the actuators can be rotated manually by a user's hand.

Various embodiments of an alternative retractor system are shown in FIGS. 17-24. The retractor system 300 includes a unique attachment mechanism 368 that is capable of attaching one or more additional blades to an existing retractor system, thereby further facilitating tissue retraction.

Figure 17:
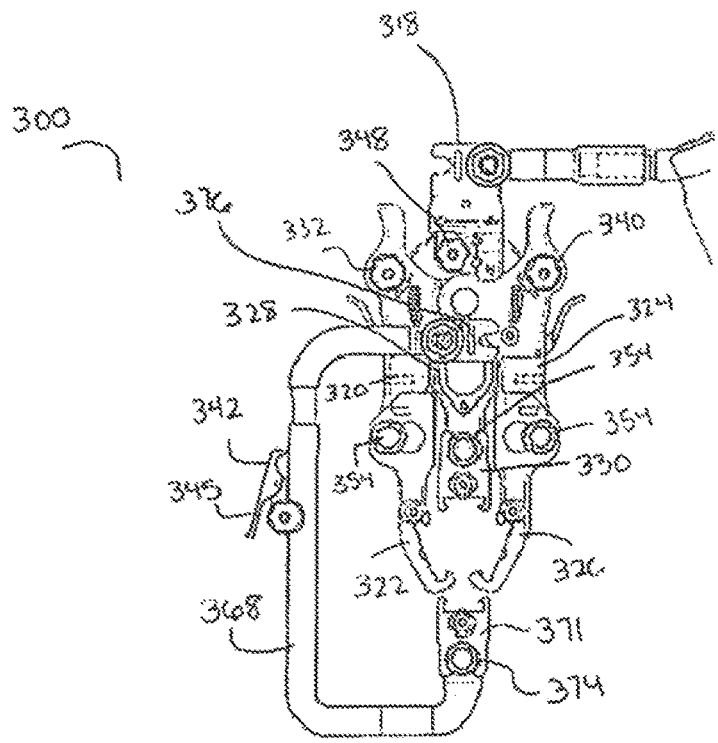
FIG. 17 illustrates a top view of an alternative retractor system with a left-handed attachment mechanism in accordance with some embodiments.

FIG. 17 illustrates a top view of an alternative retractor system with a left-handed attachment mechanism in accordance with some embodiments. The retractor system 300 comprises many similar components as the retractor system 10 in FIG. 1, including a frame 318 comprising a first rotatable arm 320 having a first blade attachment member 322 for holding and positioning a first blade, a second rotatable arm 324 having a second blade attachment member 326 for holding and positioning a second blade, and a linearly translatable arm 328 having a third blade attachment member 330. The first and second rotatable arms 320, 324 and the linearly translatable arm 328 may be actuated so that the blades (not shown) may be separated a desired distance from each other. In addition, the blade attachment members 322, 326 and 330 may be actuated to angulate the blades thereby increasing the distance between the distal ends of the blades. Further, the retractor system 300 can include an actuator 332 for the first rotatable arm 320, an actuator 340 for the second rotatable arm 324, and an actuator 348 for the linear translatable arm 328. Additional actuators 354 help to angulate the blades.

The retractor system 300 further comprises a unique attachment mechanism 368 that is capable of attaching one or more additional blades to the existing retractor system. The attachment mechanism 368 is configured to attach to an unoccupied mount 376 located on the frame 318 of the retractor system 300. In some embodiments, the mount 376 is in a substantially central portion of the retractor system 300 such that attachment of the attachment mechanism to the retractor system is strong and robust. As shown in FIG. 17, the attachment mechanism 368 includes one or more arms that extend from the mount 376. The arms can be straight or cured. A fourth blade attachment member 371 is positioned at a distal section of the attachment mechanism 368 and is configured to receive a fourth blade to assist in separation and retraction of tissue. The attachment mechanism 368 thus advantageously provides a convenient mechanism to attach additional blades to retractor systems, thereby enhancing the efficacy of a desired retraction. If an additional blade is desired, a user such as a surgeon can simply attach the attachment mechanism 368 to a mount on the existing retractor system to thereby enhance tissue separation.

In some embodiments, portions of the attachment mechanism 368, such as the fourth blade attachment member 371, can have translated motion. Translated motion can be performed using a rack and pinion configuration 345 as shown in FIG. 17. When a user presses down on the handle 345, this can result in translational motion of the fourth blade attachment member 371. In some embodiments, the attachment mechanism 368 can also include an actuator 374 for angling the fourth blade.

Figure 18:
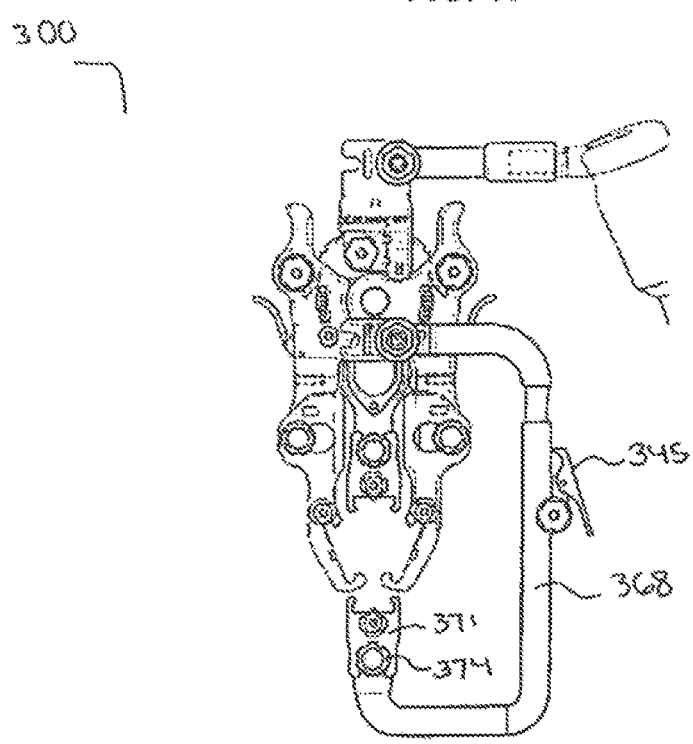
FIG. 18 illustrates a top view of an alternative retractor system with a right-handed attachment mechanism for an opposite hand in accordance with some embodiments.

In the illustrated embodiment, the attachment mechanism 368 is suitable for use by a left-handed user. As shown in FIG. 18, the attachment mechanism 368 can also be configured for use by a right-handed user, thereby having increased versatility.

While the illustrated embodiments show a single attachment mechanism 368 for adding a fourth blade, more than one attachment mechanism can be provided to add two, three, four or more blade members.

Figure 19:
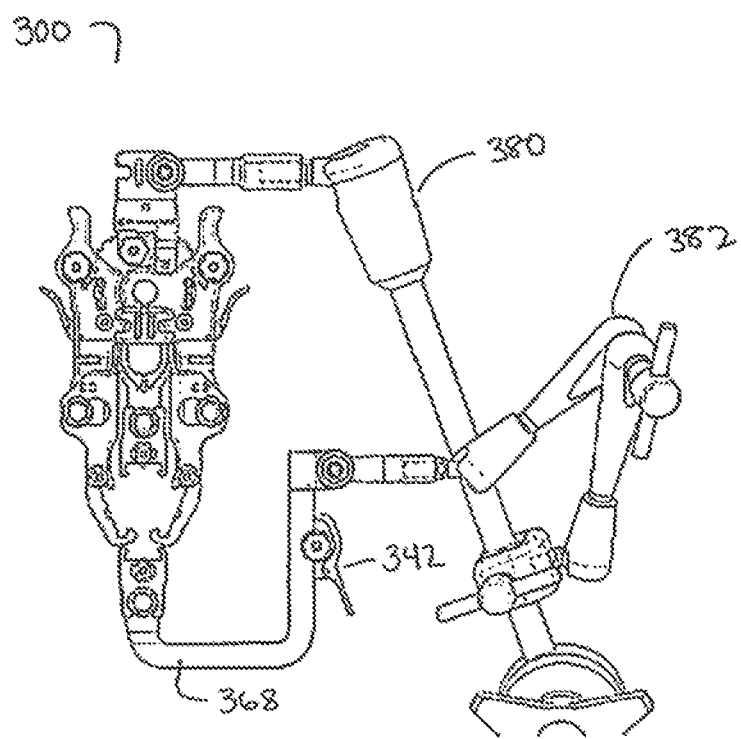
FIG. 19 illustrates a top view of an alternative retractor system with an attachment mechanism having a frame with a multi-axial adjustment mechanism in accordance with some embodiments.

FIG. 19 illustrates a top view of an alternative retractor system with an attachment mechanism having a frame with a multi-axial adjustment mechanism in accordance with some embodiments. The retractor system 300 includes an attachment mechanism 368 in a "J-configuration" having a fourth blade attachment member 371. Translational movement of the fourth blade attachment member can be performed using a rack and pinion system 342.

Advantageously, as shown in FIG. 19, the retractor system 300 is operatively coupled to a long arm 380 and short arms 382. The long arm 380 and short arms 382 can be used to position portions of the retractor system 300 in different orientations and angles. The illustrated system 300 thus provides more freedom to users in how to position the retractor system 300 in space in a controlled manner.

Figure 20:
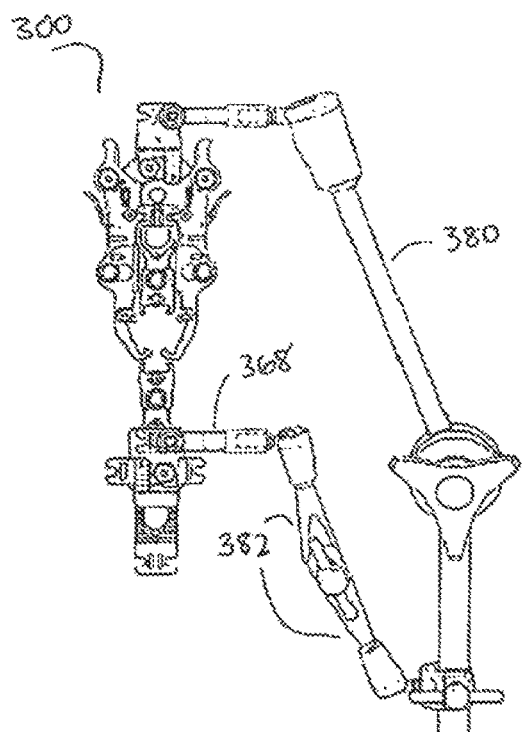
FIG. 20 illustrates a top view of an alternative retractor system with an attachment mechanism having a different frame with a multi-axial adjustment mechanism in accordance with some embodiments.

FIG. 20 illustrates a top view of an alternative retractor system with an attachment mechanism having a different frame for multi-axial adjustment in accordance with some embodiments. The retractor system 300 includes a long arm 380 and short arms 382 in a different configuration from that in FIG. 19. The illustrated embodiment thus shows the variability in orientation and placement of the attachment mechanism 368 that is provided by having long and short arms.

Figure 21:
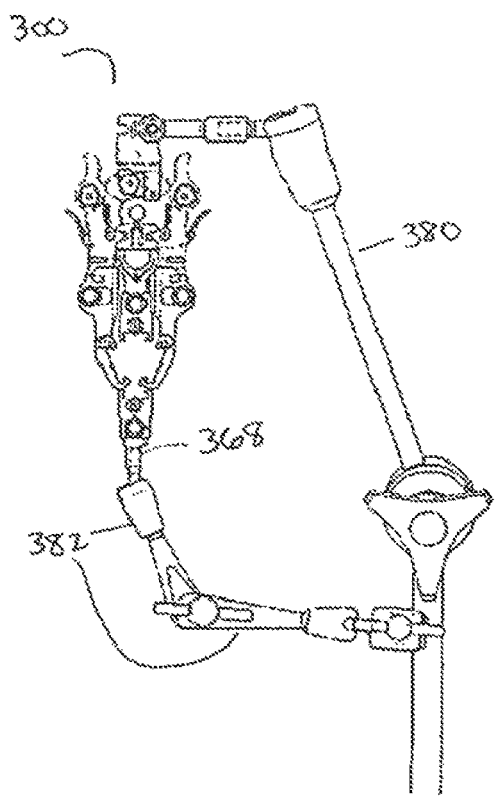
FIG. 21 illustrates a top view of an alternative retractor system with an attachment mechanism having a different frame with a multi-axial adjustment mechanism in accordance with some embodiments.

FIG. 21 illustrates a top view of an alternative retractor system with an attachment mechanism having a different frame with a multi-axial adjustment mechanism in accordance with some embodiments. The retractor system 300 includes a long arm 380 and shorts arms 382. In this embodiment, the short arms 382 are configured to assist in fixing the location of the fourth blade within the system.

Figure 22:
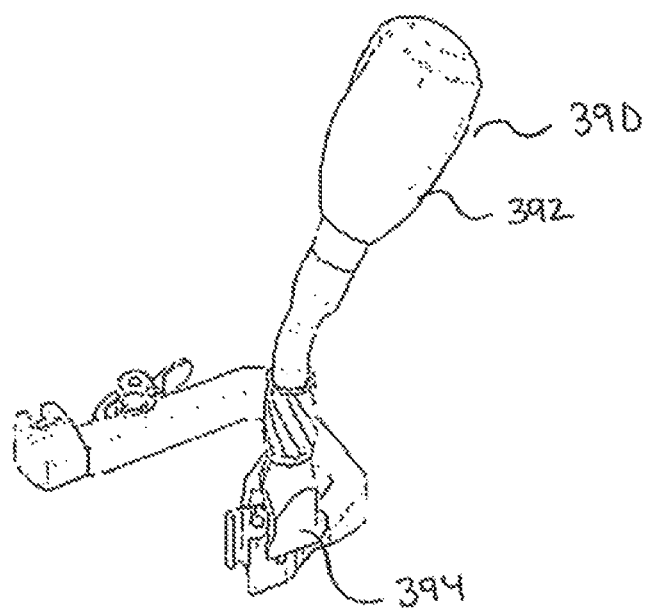
FIG. 22 illustrates a perspective view of a segment of a retractor system comprising a handle in accordance with some embodiments.
Figure 23:
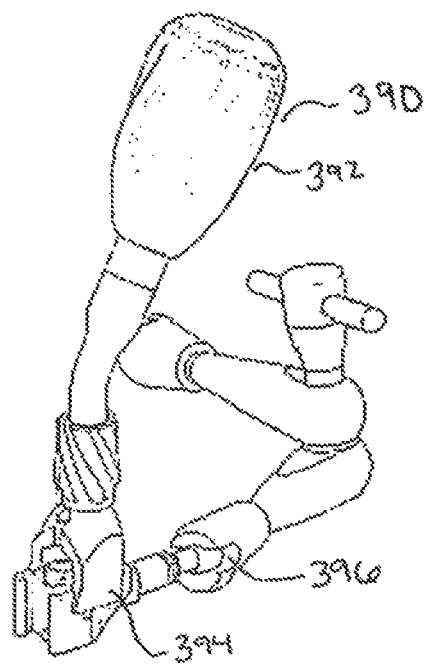
FIG. 23 illustrates a perspective view of an alternative segment of a retractor system comprising a handle in accordance with some embodiments.
Figure 24:
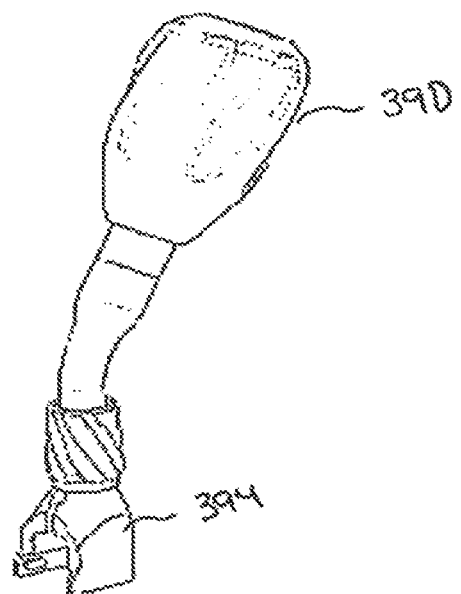
FIG. 24 illustrates a perspective view of an alternative segment of a retractor system comprising a handle in accordance with some embodiments.

FIGS. 22-24 illustrate perspective views of a handle portion of a retractor system according to some embodiments. As shown in FIG. 22, the handle portion 390 includes a handle 392 and a clamp member 394 that is capable of clamping onto different arms of the retractor system 300. Additional clamp members 396 can also be provided to adjust the position and orientation of the arms, as shown in FIG. 23. By applying a force to the handle portion 390, the arms of the retractor system 300 can assume various positions and orientations. With such handle portions, the retractor system can advantageously provide a multitude of angle adjustments in a controlled manner.

Various embodiments of an alternative retractor system having two blades are shown in FIGS. 27-40. The blades advantageously comprise one or more slots to receive pins, shims, or other components to assist in a retraction procedure.

Figure 25:
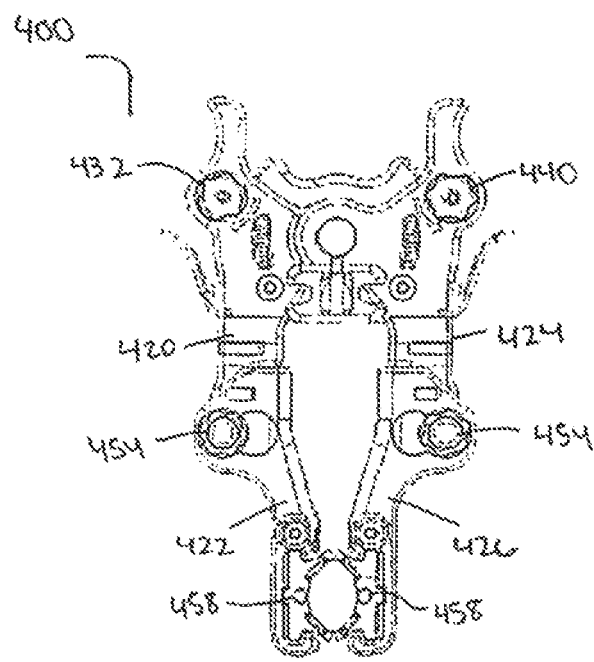
FIG. 25 illustrates a top view of a two-blade retractor system according to some embodiments.

FIG. 25 illustrates a top view of a two-blade retractor system according to some embodiments. The retractor system 400 comprises a first rotatable arm 420 including a first blade attachment member 422 and a second rotatable arm 424 including a second blade attachment member 426. A first blade 412 can be attached to the first blade attachment member 422, while a second blade 414 can be attached to the second attachment member 424. The first rotatable arm 420 can be actuated by rotation of actuator 432, while the second rotatable actuator 424 can be actuated by rotation of actuator 440. Additional actuators 454 can be provided to angulate blades attached to the blade attachment members. The retractor system 400 further includes a pair of holes 58 that can be configured to allow passage of light components, k-wires, or other suitable instruments through the blades 412, 414.

Figure 28:
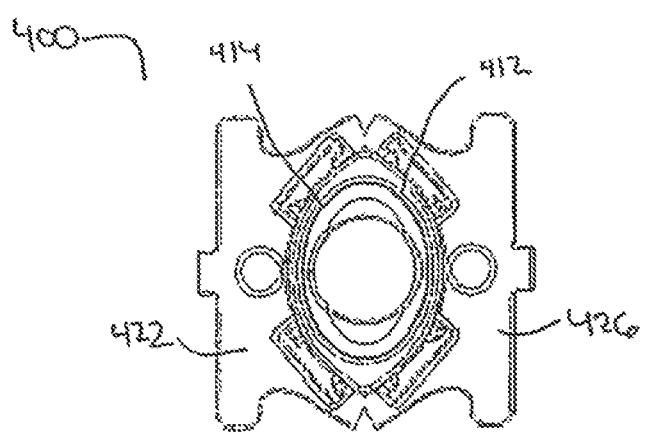
FIG. 28 illustrates a top view of a pair of blade attachment members of the retractor system in FIG. 25.

The pair of blade attachment members are configured to receive the first blade 412 and the second blade 414 as shown in FIG. 28. Advantageously, the blade attachment members are configured to receive the blades 412 and 414 such that the two blades are opposed and form a compact oval shape in the retractor's closed position. Advantageously, the two blades are capable of simple separation and contraction via movement of the actuators 432 and 440.

Figure 26:
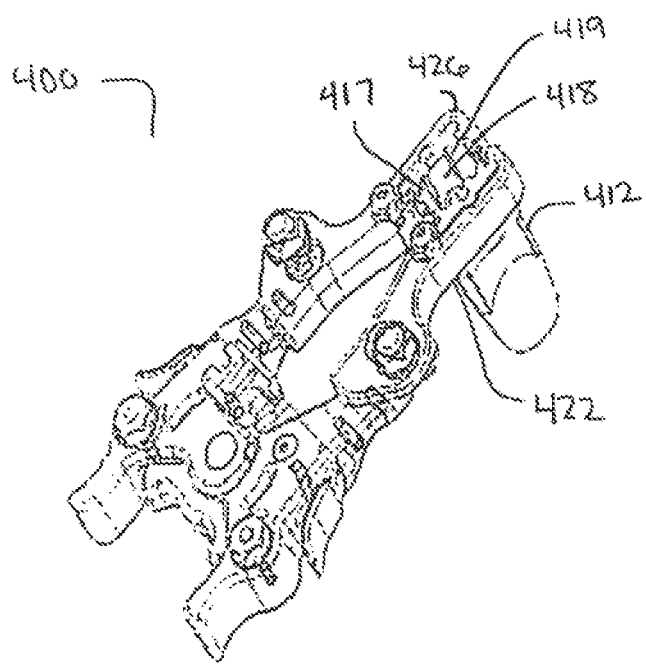
FIG. 26 illustrates a perspective view of the two-blade retractor system in FIG. 25.
Figure 27:
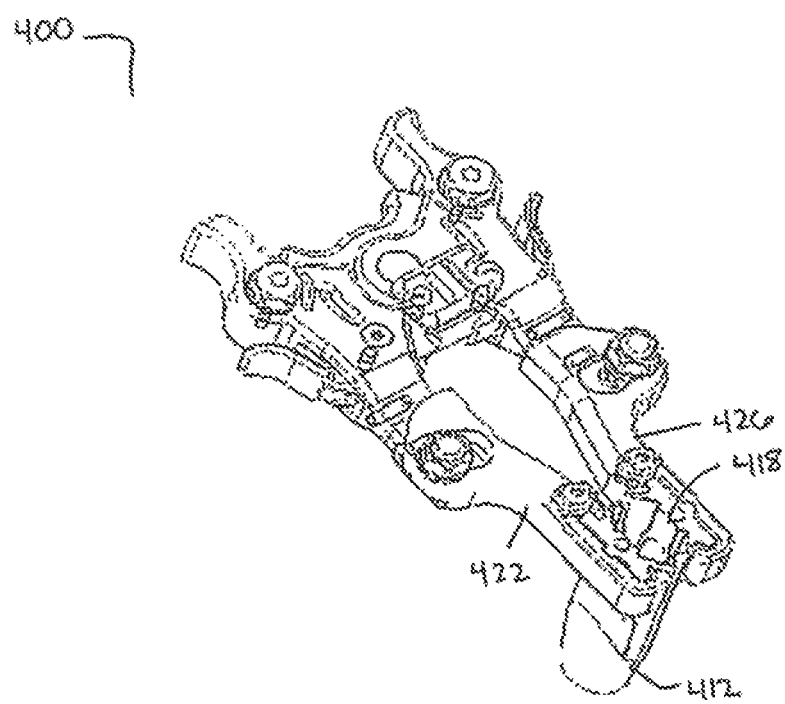
FIG. 27 illustrates a different perspective view of the two-blade retractor system in FIG. 25.

FIGS. 26 and 27 illustrate additional perspective views of the two-blade retractor system in FIG. 25. From these viewpoints, a first blade 412 is shown attached to the blade attachment member 426. The first blade 412 advantageously includes an inner channel 418 including one or more insertion grooves 417, 419. Additional components, such as the shim member 480 in FIG. 36, can be advantageously attached to the first blade 412 via the grooves in the inner channel. For example, to attach the shim member 480 to the first blade 412, wings 481, 482 of the shim member 480 (shown in FIG. 36) can be downwardly inserted into the grooves 417, 419 in the blade, thereby resulting in the assemblies shown in FIG. 35. The shim member 480 includes an opening 484 for receiving an anchor member 436, which can be secured into a bone member. More details regarding the shim member 480 and its advantages are discussed below.

FIG. 28 illustrates a top view of the blade attachment members 412 and 414. From this viewpoint, the distinct oval shape formed by the attachment members 412, 414 is clearly shown.

Figure 29:
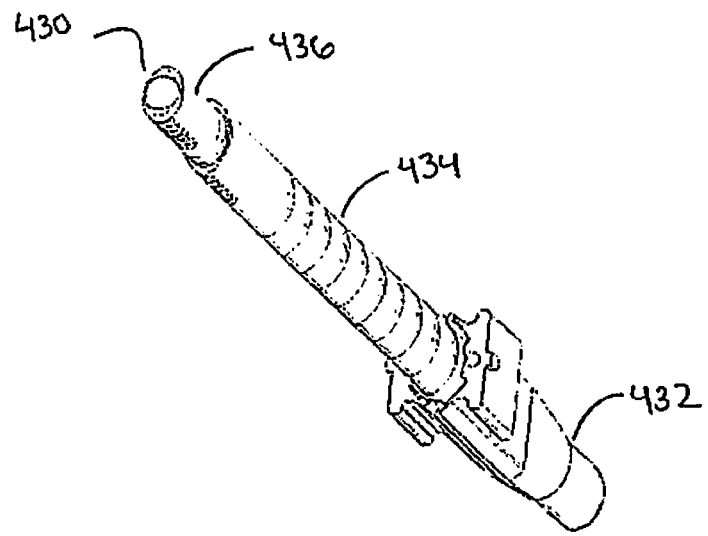
FIG. 29 illustrates a perspective view of a dilator according to some embodiments.

FIG. 29 illustrates a perspective view of a dilator for use with the retractor system in FIG. 25. The dilator 430 comprises a handle 432 operably attached to dilating outer tube 434 and dilating inner tube 436. Advantageously, the dilator tubes 434, 436 are oval shaped to accommodate the shape of the retractor system's blade attachment members 422, 426 in their closed position.

Figure 30:
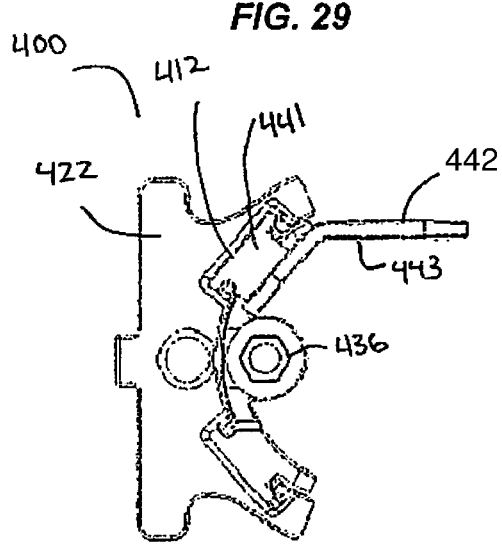
FIG. 30 illustrates a top view of a blade attachment member including an extension member and a shim member with an anchor member according to some embodiments.

FIG. 30 illustrates a top view of a blade attachment member having a blade member with an extension portion attached thereto according to some embodiments. The extension portion 442, shown on its own in FIGS. 39 and 40, comprises an insertion portion 441 and blocking member 443. As shown in FIG. 30, the insertion portion 441 is capable of sliding into the channel of the blade 412, thereby operably connecting the extension portion 442 to the blade 412. When the retractor 400 is expanded into an open configuration from its closed position, the pair of blades attached to the blade attachment members will separate from one another and expand outwardly. The separation of the blades results in a gap between the two blades. Advantageously, by affixing one or more extension portions 442 to the blades, the one or more extension portions can serve as a barricade for the gaps, thereby preventing undesired tissue from entering through the gaps into the retractor system.

Figure 35:
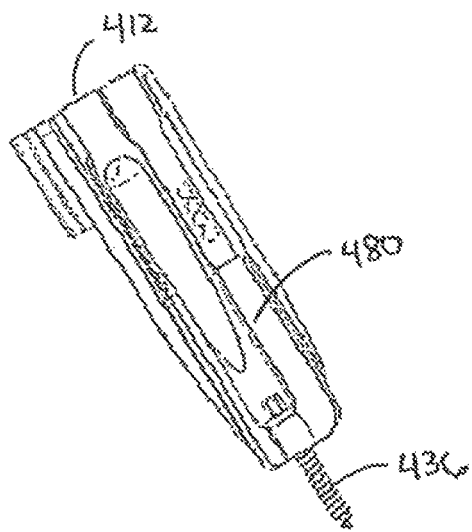
FIG. 35 illustrates a front perspective view of the blade of FIG. 33.
Figure 36:
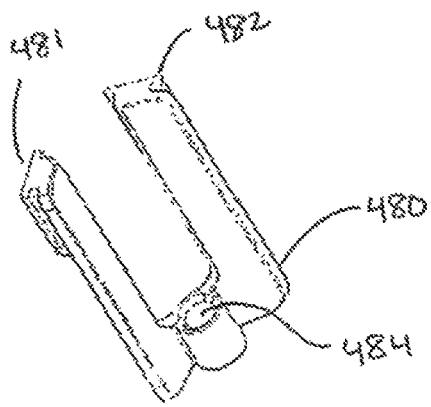
FIG. 36 illustrates a side perspective view of a shim member according to some embodiments.

In the embodiment in FIG. 30, the retractor system 400 further includes a shim member for receiving an anchor member 436. The shim member can be inserted into the channel of the blade as shown in FIGS. 35 and 36.

Figure 31:
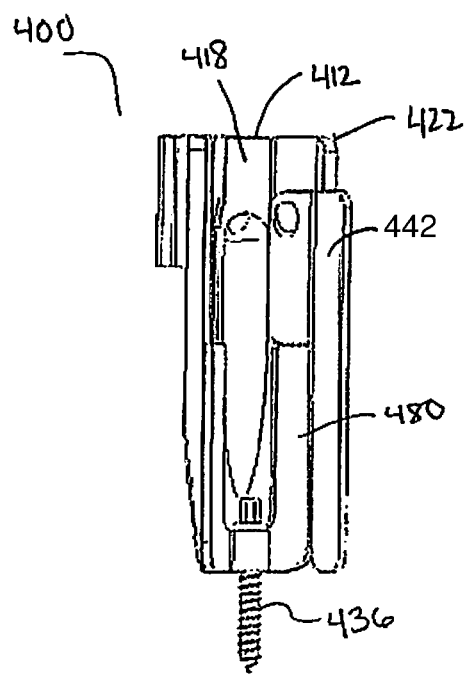
FIG. 31 illustrates a side view of a blade including an extension portion and a shim member according to some embodiments.
Figure 32:
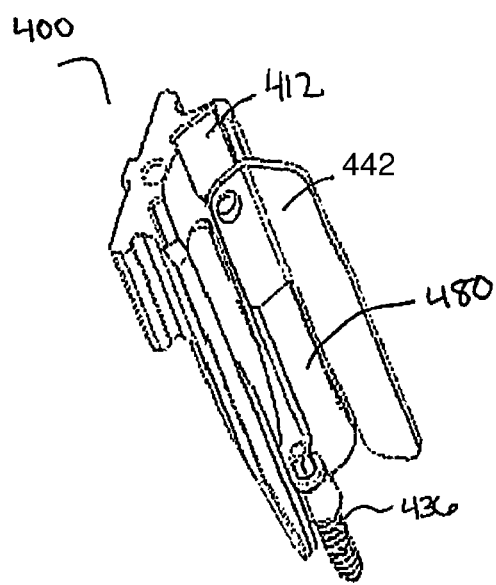
FIG. 32 illustrates a top perspective view of the blade of FIG. 31.

FIGS. 31 and 32 illustrate different views of a first blade including the extension portion 442 and shim member 480. From these views, the attachment of the shim member 480 and the extension member 442 to the blade 412 is clearly shown.

As shown in the figures, the shim member 480 can be inserted through the channel 418 of the blade 412. The shim member 480 is configured to receive the anchor member 436, which can anchor the blade, and thus the retractor system 400, to a bone member. Advantageously, when the retractor system 400 is anchored to a bone member via the anchor member 436, the retractor system 400 can use the anchor member 436 as leverage during the expansion and opening of the retractor blades. It has been found that using an anchor member 436 with a diameter of at least 3.0 mm will serve as a suitable anchor that will reduce the risk of breaking of the anchor member during the opening of the retractor blades.

After the shim member 480 is positioned in the blade 412, the extension portion 442 can then be attached to the blade 412. The insertion portion 441 of the extension portion 442 can be downwardly inserted through the grooves of the blade 412. As shown in FIGS. 31 and 32, in some embodiments, the extension portion 442 can rest on top of a portion of the shim member 480 that is positioned in the grooves of the blade. One skilled in the art will appreciate that while FIGS. 31 and 32 illustrate both a shim member 480 and an extension portion 442 attached to the blade, the use of either of the shim member and the extension portion is optional.

Figure 33:
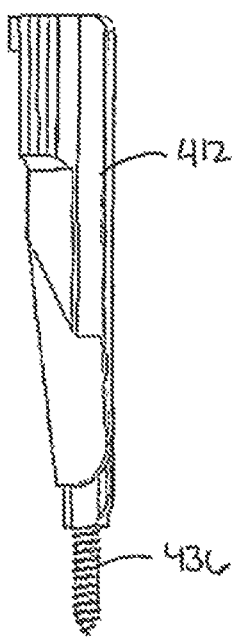
FIG. 33 illustrates a back view of the blade including an anchor member according to some embodiments.
Figure 34:
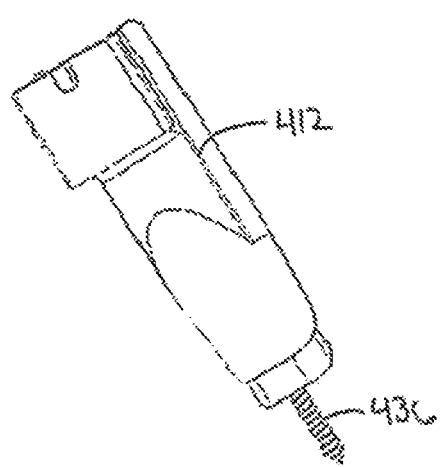
FIG. 34 illustrates a back perspective view of the blade of FIG. 33.

FIGS. 33-35 illustrate different views of a blade with an anchor member attached thereto. As shown in the figures, the anchor member 436 extends from a distal portion of the blade 412, such that the anchor member 436 is capable of fixation into a bone member, such as a vertebral body.

Figure 37:
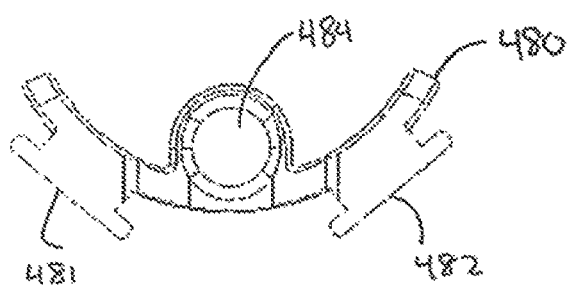
FIG. 37 illustrates a top view of the shim of FIG. 36.
Figure 38:
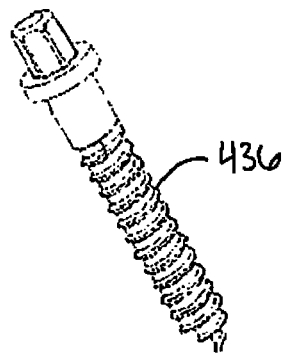
FIG. 38 illustrates the anchor member according to one embodiment of the invention.
Figure 39:
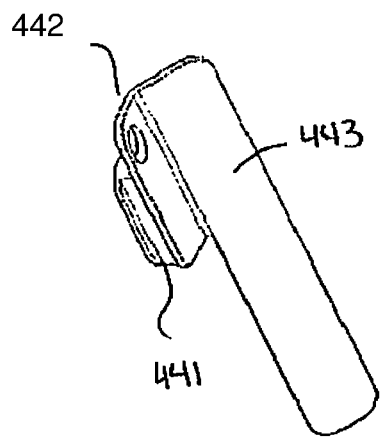
FIG. 39 illustrates the extension portion according to one embodiment of the invention.
Figure 40:
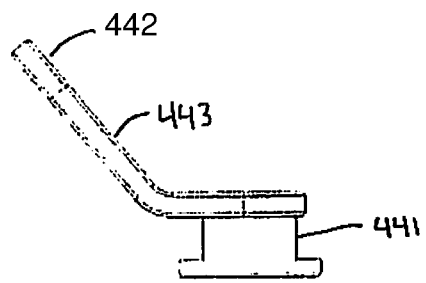
FIG. 40 illustrates the top view of the extension portion of FIG. 39.

FIGS. 36 and 37 illustrate different views of a shim member according to some embodiments. The shim member 480 includes wings 481, 482 that are capable of inserting into grooves of a blade. The shim member 480 further includes opening 484 for receiving an anchor member.

The retractor system in FIGS. 25-40 can operate as follows. A dilator having a plurality of tubes can be inserted adjacent a surgical site. The dilator's tubes can be oval, as shown in FIG. 29. Following the use of the dilator, a retractor system as shown in FIG. 25 can be provided. The retractor system is configured to include at least two blade attachment members that each attach to a blade member. In the retractor's closed position, the blade members form an oval opening. By turning actuators on the retractor, the blade members can be configured to open and close, as well as angulate, to assist in retraction of tissue. Optionally, a shim member is provided in one or more of the blade members to receive an anchor member. The shim member can be slidably inserted down one or more of the blade members. In some embodiments, the anchor member can have a diameter of 3 mm or greater. The anchor member can be inserted into the shim member and through a vertebral body, thereby helping to provide leverage while the retractor blades are expanded. Optionally, an extension member can be provided that serves as a barricade to gaps upon extension of the retractor blades.

While it is apparent that the invention disclosed herein is well calculated to fulfill the objects stated above, it will be appreciated that numerous modifications and embodiments may be devised by those skilled in the art.

What is claimed is:

1. A multi-blade retractor system comprising:
a retractor frame comprising a first arm and a second arm;
a first blade coupled to a distal end of the first arm, the first blade having a first channel; and
a second blade coupled to a distal end of the second arm;
wherein the first blade includes an anchor member receiving portion at a distal end of the first blade, the anchor member receiving portion slidably received in the first channel of the first blade,
wherein the anchor member receiving portion is configured to receive an anchor member capable of fixation into a bone member, and
an extension portion slidably received in the first channel of the first blade such that the extension portion directly rests atop the anchor member receiving portion
wherein the first blade has a second channel, the anchor member receiving portion is slidably received in the second channel of the first blade, but the extension portion is not received in the second channel of the first blade.

2. The retractor system of claim 1, wherein the first arm is rotatable.

3. The retractor system of claim 2, wherein the second arm is rotatable.

4. The retractor system of claim 1, wherein the anchor member receiving portion is removable from the first blade.

5. A multi-blade retractor system comprising:
- a retractor frame comprising a first arm and a second arm;
- a first blade coupled to a distal end of the first arm, the first blade having a first channel;
- a second blade coupled to a distal end of the second arm;
- wherein the first blade and the second blade each include an anchor member receiving portion at a distal end, one of the anchor member receiving portions slidably received in the first channel of the first blade,
- wherein the anchor member receiving portion is configured to receive an anchor member capable of fixation into a bone member, and
- an extension portion slidably received in the first channel of the first blade such that the extension portion directly rests atop the anchor member receiving portion
- wherein the first blade has a second channel, the anchor member receiving portion is slidably received in the second channel of the first blade, but the extension portion is not received in the second channel of the first blade.

6. The retractor system of claim 5, wherein the first arm is rotatable.

7. The retractor system of claim 6, wherein the second arm is rotatable.

8. The retractor system of claim 5, wherein the anchor member receiving portion is removable from the first blade and second blade.

* * * * *